(12) United States Patent
Zapf et al.

(10) Patent No.: US 6,291,383 B1
(45) Date of Patent: Sep. 18, 2001

(54) PROCESS FOR PREPARING AROMATIC OLEFINS IN THE PRESENCE OF PALLADIUM CATALYSTS COMPRISING PHOSPHITE LIGANDS

(75) Inventors: Alexander Zapf, Rosenheim; Thomas Riermeier, Frankfurt; Matthias Beller, Rostock, all of (DE)

(73) Assignee: Aventis Research & Technologies GmbH & Co. Kg (DE)

( * ) Notice: Subject to any disclaimer, the term of this patent is extended or adjusted under 35 U.S.C. 154(b) by 0 days.

(21) Appl. No.: 09/326,404

(22) Filed: Jun. 4, 1999

(30) Foreign Application Priority Data

Jun. 6, 1998 (DE) .............................. 198 25 454

(51) Int. Cl.[7] .............................. B01J 31/00; C08F 4/02

(52) U.S. Cl. ........................................... 502/103

(58) Field of Search .............................. 502/103

(56) References Cited

PUBLICATIONS

Chadwick A. Tolman, "Steric Effects of Phosphorus Ligands in Organometallic Chemistry and Homogeneous Catalysis", (1976) pp. 313–348.
Meijere et al., "Kleider machen Leute: Heck–Reaktion im neuen Gewand", Agnew Chem. (1994), pp. 2473–2506.
Wolfgang A. Herrmann, "3.1.6 Catalytic Carbon—Carbon Coupling by Palladium Complexes: Heck Reactions" vol. 2, VCH Weinheim (1996) pp. 712–732.
Richard F. Heck, "Palladium–Catalyzed Vinylation of Organic Halides", (1976), pp. 345–391.
Beller, et al., "Palladacyclen als effiziente Katalysatoren für Arylkupplungsreaktionen", Angew, Chem. (1995), 107, Nr. 17 p. 1989–1992.
L. Honig, "Preparation of Polymer–Supported Catalysts . . . Vinylation Reaction", Reactive Polymers 16 (1991/1992, pp. 181–197).
M. Beller, "Phosphites as Ligands for Efficient Catalysis of Heck Reaction", Nr. 7, Jul. 1998 (1998–97), pp. 792–793; XP–002112145.

Primary Examiner—Mukund J. Shah
Assistant Examiner—Sudhaker B. Patel
(74) Attorney, Agent, or Firm—Connolly Bove Lodge & Hutz LLP

(57) ABSTRACT

The invention relates to process for preparing monofunctional, bifunctional or/and polyfunctional olefins of the formulae (Ia), (Ib), (Ic) or/and (Id),

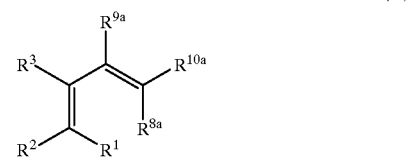
(Ia)

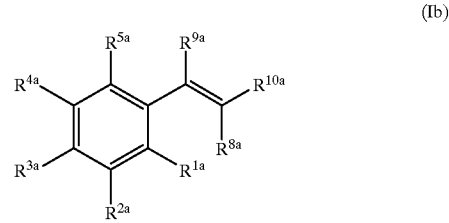

(Ib)

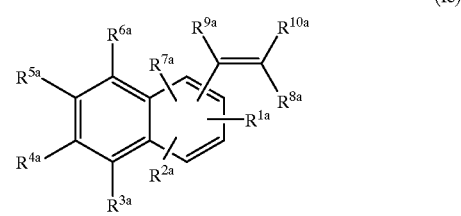

(Ic)

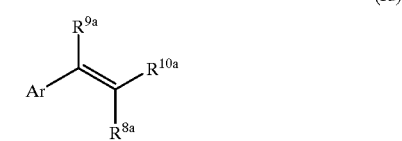

(Id)

where $R^1$ to $R^3$ are, independently of one another, hydrogen, $(C_1-C_8)$-alkyl, CN, COOH, COO-alkyl-$(C_1-C_8)$, CO-alkyl-$(C_1-C_8)$, aryl-$(C_6-C_{10})$, COO-aryl-$(C_{6-C10})$, CO-aryl-$(C_6-C_{10})$, O-alkyl-$(C_1-C_8)$, O—CO-alkyl-$(C_1-C_8)$ or N-alkyl$_2$-$(C_1-C_8)$ and aryl is an aromatic radical containing up to 14 carbon atoms, where aryl is as defined above, and Ar is a heteroaromatic, by reacting haloaromatics, haloolefins or/and heterohaloaromatics of the formulae (IIa), (IIb), (IIc) or/and (IId) with olefins of the formula (III), wherein a mixture of a palladium(0) complex or a palladium(II) salt with phosphite ligands of the formulae (IVa) or/and (IVb)

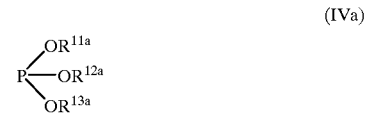

(IVa)

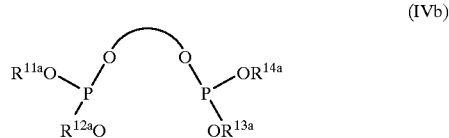

(IVb)

is used as catalyst.

19 Claims, No Drawings

PROCESS FOR PREPARING AROMATIC OLEFINS IN THE PRESENCE OF PALLADIUM CATALYSTS COMPRISING PHOSPHITE LIGANDS

The present invention relates to a process for preparing aromatic olefins using palladium catalyst systems comprising phosphite ligands.

Olefins, in particular aromatic olefins such as cinnamic acid derivatives, styrenes or stilbenes, are of industrial importance as fine chemicals, starting materials for polymers, UV absorbers, agrochemicals and precursors of active compounds.

A frequently employed method of synthesizing aromatic olefins in the university sector is the Heck reaction in which iodoaromatics or bromoaromatics and, in exceptional cases, chloroaromatics are reacted with olefins in the presence of palladium catalysts. Reviews which describe this methodology may be found, for example, in R. F. Heck, Org. React. 1982, 27, 345 and in B. Cornils, W. A. Herrmann, Applied homogeneous catalysis with organometallic compounds, Vol. 2, p. 712, VCH, Weinheim 1996.

Catalysts which are used for the purposes of the Heck reaction are palladium compounds. Although both palladium (II) and palladium(0) complexes can be used in Heck reactions, it is generally accepted that palladium(0) compounds are the actual catalysts in the reaction. In particular, co-ordinatively unsaturated 14 and 16 electron palladium(0) species which are stabilized by means of donor ligands such as phosphines are formulated in the literature. When using aryl iodides as starting materials in Heck reactions, it is also possible to dispense with phosphine ligands. However, aryl iodides are very expensive starting compounds which, moreover, produce stoichiometric amounts of waste iodide salts. Less expensive starting materials for the Heck reaction, e.g. aryl bromides or aryl chlorides, require the addition of stabilizing ligands for them to be catalytically activated and reacted.

The catalyst systems described for Heck reactions frequently give satisfactory catalytic turnover numbers (=TONs) only when uneconomical starting materials such as iodoaromatics and activated bromoaromatics are used. Otherwise, in the case of deactivated bromoaromatics and particularly in the case of chloroaromatics, it is generally necessary to add large amounts of catalyst, customarily from 1 to 5 mol%, in order to achieve industrially useful conversions. In addition, owing to the complexity of the reaction mixtures, simple catalyst recycling is not possible, so that the catalyst costs generally also stand in the way of industrial implementation. Although newer catalyst systems based on cyclometallated phosphines give satisfactory catalyst activities for a series of bromoaromatics, the catalyst have to be prepared separately from expensive alkylated phosphines. Furthermore, chloroaromatics cannot yet be activated in an industrially satisfactory manner using these catalysts (W. A. Herrmann, C. Broβmer, K. Öfele, T. Priermeier, M. Beller, H. Fischer, Angew. Chem. 1995, 107, 1989, Strukturell definierte Katalysatoren für die Heck-Olefinierung von Chlor—und Bromaromaten). Where high yields were achieved, it was necessary to use very high and thus very expensive amounts of catalyst since the catalyst TON has hitherto been low even using these systems.

For these reasons, there is a great need for a new palladium catalyst system which comprises inexpensive ligands and which does not display the disadvantages of the known catalytic processes, which is suitable for industrial-scale use and which gives olefins in high yield and purity with a high catalyst TON.

This object is achieved by a process for preparing monofunctional, bifunctional or/and polyfunctional olefins of the formulae (Ia), (Ib), (Ic) or/and (Id),

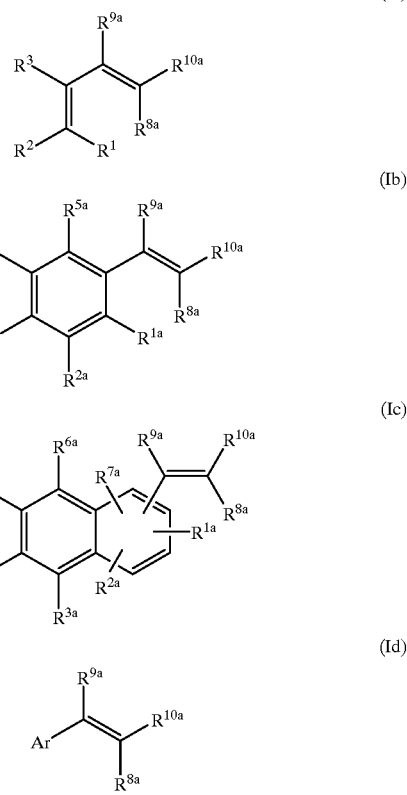

where $R^1$ to $R^3$ are, independently of one another, hydrogen, $(C_1–C_8)$-alkyl, CN, COOH, COO-alkyl-$(C_1–C_8)$, CO-alkyl-$(C_1–C_8)$, aryl-$(C_6–C_{10})$, COO-aryl-$(C_6–C_{10})$, CO-arly-$(C_6–C_{10})$, O-alkyl-$(C_1–C_8)$, O—CO-alkyl-$(C_1–C_8)$, N-alkyl $_2$-$(C_1–C_8)$ and aryl is an aromatic radical containing up to 14 carbon atoms, where this radical may bear up to five substituents which are, independently of one another, hydrogen, $(C_1–C_8)$-alkyl, O-alkyl-$(C_1–C_8)$, OCO-alkyl-$(C_1–C_8)$, O-phenyl, phenyl, aryl, fluorine, chlorine, OH, $NO_2$, Si(alkyl-$(C_1–C_8)$)$_3$, CN, COOH, CHO, $SO_3H$, $NH_2$, NH-alkyl-$(C_1–C_8)$, N-alkyl$_2$-$(C_1–C_8)$, P-alkyl$_2$-$(C_1–C_6)$, $SO_2$-alkyl-$(C_1–C_6)$, SO-alkyl-$(C_1–C_6)$, $CF_3$, NHCO-alkyl-$(C_1–C_4)$, COO-alkyl-$(C_1–C_8)$, $CONH_2$, CO-alkyl-$(C_1–C_8)$, NHCOH, NHCOO-alkyl-$(C_1–C_4)$, CO-phenyl, COO-phenyl, CHCH—$CO_2$-alkyl-$(C_1–C_8)$, P(phenyl)$_2$, CHCHCO$_2$H, PO-phenyl$_2$, POalkyl$_2$-$(C_1–C_4)$, $PO_3H_2$, PO(O-alkyl-$(C_1–C_6)$)$_2$, $SO_3$-alkyl-$(C_1–C_4)$, where aryl is as defined above, and where $R^{1a}$ to $R^{7a}$ are, independently of one another, hydrogen, $(C_1–C_8)$-alkyl, O-alkyl-$(C_1–C_8)$, OCO-alkyl-$(C_1–C_8)$, O-phenyl, phenyl, aryl, fluorine, chlorine, OH, $NO_2$, Si(alkyl-$(C_1–C_8)$)$_3$, CN, COOH, CHO, $SO_3H$, $NH_2$, NH-alkyl-$(C_1–C_8)$, N-alkyl $_2$-$(C_1–C_8)$, P-alkyl $_2$-$(C_1–C_8)$, $SO_2$-alkyl-$(C_1–C_6)$, SO-alkyl-$(C_1–C_6)$, $CF_3$, NHCO-alkyl-$(C_1–C_4)$, COO-alkyl-$(C_1–C_8)$, $CONH_2$, CO-alkyl-$(C_1–C_8)$, NHCOH, NHCOO-alkyl-$(C_1–C_4)$, CO-phenyl, COO-phenyl, CHCH—CO$_2$-alkyl-(C$_1$–C$_8$), P(phenyl)$_2$, CHCHCO$_2$H, PO-phenyl$_2$-(C$_1$–C$_4$), PO$_3$H$_2$, PO(O-alkyl-(C$_1$–C$_6$))$_2$, SO$_3$-alkyl-(C$_1$–C$_4$), where aryl is as defined above and where Ar is a heteroaromatic, where the heteroaromatic Ar can be a substituted five-, six- or seven-membered ring containing, if desired, nitrogen, oxygen or sulfur atoms in the ring, where further aromatic, heteroaromatic and/or aliphatic rings can be fused onto the ring, and where the heteroaromatic can have substituents which are, independently of one another, hydrogen, (C$_1$–C$_8$)-alkyl, O-aryl, aryl, fluorine, chlorine, OH, NO$_2$, CN, CO$_2$H, CHO, SO$_3$H, NH$_2$, NH-alkyl-(C$_1$–C$_2$), N-alkyl$_2$-(C$_1$–C$_{12}$), CHCHCO$_2$H, NHCO-alkyl-(C$_1$–C$_{12}$), CO-alkyl-(C$_1$–C$_{12}$), NHCHO, COaryl, CO$_2$aryl, CF$_3$, CONH$_2$, POaryl$_2$, POalkyl$_2$-(C$_1$–C$_{12}$), Si(alkyl-(C$_1$–C$_{12}$))$_3$, O-alkyl-(C$_1$–C$_8$), OCO-alkyl-O-phenyl, phenyl, NH-alkyl-(C$_1$–C$_4$), COO-alkyl-(C$_1$–C$_8$), NHCOO-alky-(C$_1$–C$_4$), CO-phenyl, COO-phenyl, CHCH—CO$_2$-alkyl-(C$_1$–C$_8$), PO-phenyl$_2$, PO$_3$H$_2$, SO$_3$-alkyl-(C$_1$–C$_4$), SO$_2$-alkyl-(C$_1$–C$_4$), SO-alkyl-(C$_1$–C$_4$), where aryl is as defined above, and where R$^{8a}$ to R$^{10a}$ are, independently of one another, hydrogen, CN, CO$_2$H, CO$_2$-alkyl-(C$_1$–C$_8$), CONH$_2$, CONH-alkyl-(C$_1$–C$_4$), CON-(alkyl)$_2$-(C$_1$–C$_4$), fluorine, CO$_2$-phenyl, alkyl-(C$_1$–C$_8$), phenyl, aryl, PO(phenyl)$_2$, PO[alkyl-(C$_1$–C$_4$)]$_2$, CO-phenyl, CO-alkyl-(C$_1$–C$_4$), O-alkyl-(C$_1$–C$_4$), CONH-alkyl-(C$_1$–C$_8$), CON[alkyl-(C$_1$—C$_8$)]$_2$, NH-alkyl-(C$_1$–C$_4$), PO$_3$H$_2$, SO$_3$H, SO$_3$-alkyl-(C$_1$–C$_4$), SO$_2$-alkyl-(C$_1$–C$_4$), O-phenyl, where aryl is as defined above, by reacting haloaromatics, haloolefins or/and heterohaloaromatics of the formulae (IIa), (IIb), (IIc) or/and (IId)

(IIa)

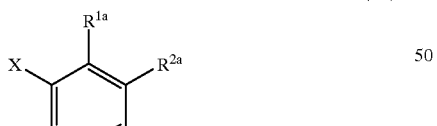
(IIb)

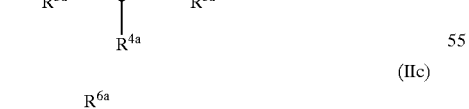
(IIc)

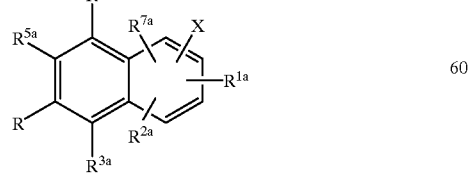

Ar—X (IId)

with olefins of the formula (II),

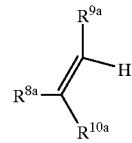
(III)

where, in the formulae of the type II and III, R$^1$ to R$^3$ and R$^{1a}$ to R$^{10a}$ are as defined above for the forrnulae of the type (I) and where X is iodine, bromine, chlorine, OSO$_2$CF$_3$, OSO$_2$-phenyl, OSO$_2$-tolyl, OSO$_2$-alkyl-(C$_1$–C$_8$), wherein a mixture of a palladium(0) complex or a palladium(II) salt with phosphylite ligands of the formulae (IVa) or/and (IVb),

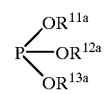
(IVa)

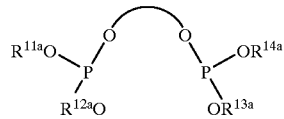
(IVb)

where the fornula (IVb) represents a chelating phosphite ligand and where the radicals R$^{11a}$ to R$^{14a}$ are identical or different and are each, independently of one another, (C$_1$–C$_{18}$)-alkyl or/and a substituted (C$_1$–C$_{18}$)-alkyl group having the substituents hydrogen, O-alkyl-(C$_1$–C$_8$), O—CO-alkyl-(C$_1$–C$_8$), O-phenyl, phenyl, fluorine, chlorine, OH, NO$_2$, CN, COOH, CHO, SO$_3$H, SO$_2$-alkyl-(C$_1$–C$_8$), SO-alkyl-(C$_1$–C$_8$), NH$_2$, NH-alkyl-(C$_1$–C$_8$), N-alkyl$_2$-(C$_1$–C$_8$), NHCO-alkyl-(C$_1$–C$_4$), CF$_3$, COO-alkyl-(C$_1$–C$_8$), CONH$_2$, CO-alkyl-(C$_1$–C$_8$), NHCOH, NHCOO-alkyl-(C$_1$–C$_4$), CO-phenyl, COO-phenyl, CHCH—CO$_2$-alkyl-(C$_1$–C$_8$), CHCHCO$_2$H, PO-phenyl$_2$, POalkyl$_2$-(C$_1$–C$_8$), or the radicals R$^{11a}$ to R$^{14a}$ are an aromatic Ar', where Ar' is a substituted phenyl, naphthyl, anthryl, phenanthryl or biphenyl radical orylland a five-, six- or seven-membered heteroaromafic containing, if desired, nitrogen, oxygen or sulfur atoms in the ring, where the aromatics may contain up to ten substituents which are (C$_1$–C$_8$)-alkyl, OAr', Ar', fluorine, chlorine, OH, NO$_2$, CN, CO$_2$H, CHO, SO$_3$H, NH$_2$, NH-alkyl-(C$_1$–C$_{12}$), N-alkyl$_2$-(C$_1$–C$_{12}$), NHCO-alkyl-(C$_1$–C$_{12}$), CO-alkyl-(C$_1$–C$_{12}$) NHCHO, COAr', CO$_2$Ar', CF$_3$, CONH$_2$, CHCHCO$_2$H, POAr'$_2$, POalkyl$_2$-(C$_{1-C12}$) Si(alkyl- (C$_1$–C$_{12}$))$_3$, O-alkyl-(C$_1$–C$_8$), OCO-alkyl-(C$_1$–C$_8$), O-phenyl, phenyl, COO-alkyl-(C$_1$–C$_8$), NHCOO-alkyl-(C$_1$–C$_4$), CO-phenyl, COO-phenyl, CHCH—CO$_2$-alkyl-(C$_1$–C$_8$), PO-phenyl$_2$, PO$_3$H$_2$, SO$_3$-alkyl-(C$_1$–C$_4$), SO$_2$-alkyl-(C$_1$–C$_4$), SO-alkyl- ($C_1$–$C_4$), where the carbon bridge of the phosphite ligand $C_2$ to $C_4$ may have up to four substituents which are identical or different and are, in particular, hydrogen, ($C_1$–$C_4$)-alkyl, O-alkyl-($C_1$–$C_4$), OH, aryl or/and phenyl, where aryl is as defined above, is used as catalyst.

In particular, compounds of the formula (Id) are prepared using, as heterohaloaromatics ArX of the formula (IId), substituted heterohaloaromatics having up to four heteroatoms such as N, O or/and S in the ring, preferably substituted pyridines, pyrimidines, oxazoles, imidazoles, pyrazines, quinolines, indoles, furans, benzofurans or/and thiophenes, where the substituents can be identical or different and be, independently of one another, hydrogen, ($C_1$–$C_8$)-alkyl, O-aryl, aryl, fluorine, chlorine, OH, $NO_2$, CN, $CO_2H$, CHO, $SO_3H$, $NH_2$, NH-alkyl-($C_1$–$C_{12}$), N-alkyl$_2$-($C_1$–$C_{12}$), NHCO-alkyl-($C_1$–$C_{12}$), CO-alkyl-($C_1$–$C_{12}$), NHCHO, COaryl, $CO_2$aryl, $CF_3$, $CONH_2$, POaryl$_2$ POalkyl$_2$-($C_1$–$C_2$), Si(alkyl-($C_1$–$C_{12}$))$_3$, O-alkyl-($C_1$–$C_8$), OCO-alkyl-($C_1$–$C_8$), O-phenyl, phenyl, COO-alkyl-($C_1$–$C_8$), NHCOO-alkyl-($C_1$–$C_4$), CO-phenyl, COO-phenyl, CHCH—$CO_2$-alkyl-($C_1$–$C_8$), PO-phenyl$_2$, $PO_3H_2$, $SO_3$-alkyl-($C_1$–$C_4$), $SO_2$-alkyl-($C_1$–$C_4$), where aryl is as defined above, and $R^{8a}$ to $R^{10a}$ can be identical or different and be, independently of one another, hydrogen, CN, $CO_2H$, phenyl, $CO_2$alkyl-($C_1$–$C_8$), $CONH_2$, F, O-alkyl-($C_1$–$C_4$), alkyl-($C_1$–$C_8$), NH-alkyl-($C_1$–$C_4$) and X can be iodine, bromine, chlorine, $OSO_2CF_3$, $OSO_2$phenyl, $OSO_2$tolyl, $OSO_2$alkyl-($C_1$–$C_8$).

Particular preference is given to a process in which olefins of the formula (Ia) in which $R^1$ to $R^3$ is hydrogen, ($C_1$–$C_4$)-alkyl or/and phenyl are prepared.

The process of the invention has been found to be particularly useful for preparing compounds of the formulae (Ia), (Ib), (Ic) or/and (Id) in which:

$R^1$ to $R^3$ and $R^{1a}$ to $R^{7a}$ are, independently of one another, hydrogen, ($C_{1-C8}$)-alkyl, O-alkyl-($C_1$–$C_8$), O—CO-alkyl-($C_1$–$C_8$), N-alkyl-($C_1$–$C_8$), phenyl, aryl, fluorine, chlorine, $NO_2$, CN, COOH, CHO, $SO_2$-alkyl-($C_1$–$C_4$), NH-($C_1$–$C_8$)-alkyl, COO-($C_1$–$C_8$)-alkyl, $CONH_2$, CO-($C_1$–$C_8$)-alkyl, CO-phenyl or/and PO-phenyl$_2$, where aryl is as defined above, and $R^{8a}$ to $R^{10a}$ are, independently of one another, hydrogen, CN, $CO_2H$, $CO_2$-alkyl-($C_1$–$C_8$), $CONH_2$, F, O-alkyl-($C_1$–$C_4$), alkyl-($C_1$–$C_8$), NH-alkyl-($C_1$–$C_4$), CONH-alkyl-($C_1$–$C_8$), CON[alkyl-($C_1$–$C_8$)]$_2$, phenyl or/and aryl, where aryl is as defined above.

The process is of particular importance for, inter alia, the preparation of compounds of the formulae (Ia), (Ib), (Ic) oryl/and (Id) in which:

$R^1$ to $R^3$ and $R^{1a}$ to $R^{7a}$ are, independently of one another, hydrogen, ($C_1$–$C_8$)-alkyl, O-alkyl-($C_1$–$C_8$), phenyl, fluorine, chlorine, $NO_2$, CN, COOH, CHO, COO-($C_1$–$C_8$)-alkyl, $CONH_2$, CO-($C_1$–$C_8$)-alkyl, CO-phenyl or/and PO-phenyl$_2$ and $R^{8a}$ to $R^{10a}$ are, independently of one another, hydrogen, CN, $CO_2H$, $CO_2$-alkyl-($C_1$–$C_8$), phenyl, $CONH_2$, F, O-alkyl-($C_1$–$C_4$), alkyl-($C_1$–$C_8$) or/and NH-alkyl-($C_1$–$C_4$).

Solvents used are generally inert organic solvents or/and water. Particularly suitable solvents are dipolar aprotic solvents such as dialkyl sulfoxides, N,N-dialkyamides of aliphatic carboxylic acids or alkylated lactams. Here, preference is given to dimethyl sulfoxide, N,N-dimethylacetamide, N,N-dimethylformamide and N-methylpyrrolidone. Other suitable solvents are aliphatic ethers, aromatic or aliphatic hydrocarbons, alcohols and esters and also mixtures thereof.

The reaction preferably proceeds at temperatures of from 20 to 200° C.; in many cases it has been found to be useful to work at temperatures of from 60 to 180° C., preferably from 100 to 160° C. The pressure can be more than 100 bar, but it is usual to work at a pressure of only up to 100 bar, preferably in the range from atmospheric pressure to 60 bar.

Since HX is eliminated in the reaction, it is advantageous to neutralize the acid formed by addition of a base. Bases which are suitable for this purpose are primary, secondary or/and tertiary amines such as alkylamines, dialkylamines, trialkylamines, which may be alicyclic or/and open-chain, or/and alkali metal or/and alkaline earth metal salts of aliphatic or/and aromatic carboxylic acids, e.g. acetates, propionates, benzoates or corresponding carbonates, hydrogencarbonates, phosphates, hydrogenphosphates or/and hydroxides, preferably of lithium, sodium, potassium, calcium, magnesium, cesium.

The palladium catalysts of the type (IV) which are used are generally generated in situ from palladium(II) salts and the corresponding phosphite ligands. However, they can also be used directly as palladium(0) phosphite complexes without the initial catalytic activity being reduced thereby. Palladium precursors which can be used are, for example: palladium(II) acetate, palladium(II) chloride, palladium(II) bromide, lithium tetrachloropalladate, palladium(II) acetylacetonate, palladium(0)-dibenzylideneacetone complexes, tetrakis(triphenylphosphine)palladium(0), bis(tri-O-tolylphosphine)palladium(0), palladium(II) propionate, bis(acetonitrile)palladium(II) chloride, bis(triphenylphosphine)palladium(II) dichloride, palladium(0)-tricyclohexylphosphine-(diallyl ether) complex, bis(tricyclohexylphosphine)-palladium(0), bis(benzonitrile) palladium(II) chloride and further palladium(0) and palladium(II) complexes. In general, the phosphite ligand is used in an excess over palladium in the present process. The ratio of palladium to ligand is preferably from 1:2 to 1:1,000. Particular preference is given to using ratios of palladium to ligand of from 1:5 to 1:200.

The use of a chelating phosphite ligand can be advantageous. Here, the carbon bridge of the phosphite ligand $C_2$ to $C_4$ has up to four substituents which are identical or different and are, in particular, hydrogen, ($C_1$–$C_4$)-alkyl, O-alkyl-($C_1$–$C_4$), OH, aryl or/and phenyl, where aryl is as defined above.

When using chloroaromatics, bromoaromatics or aryl triflates and aryl mesylates or related starting materials, it is sometimes advantageous to add a cocatalyst to the palladium phosphite catalyst. This cocatalyst is a salt of a halogen, in particular a halide of an alkali metal or/and alkaline earth metal, an ammonium halide or/and a phosphonium halide, preferably a bromide or/and chloride. Particular preference is given to LiBr, LiCI, NaBr, KBr, CsBr, Bu$_4$NCI, BU$_4$NBr, BzMe$_3$NBr, trioctylmethylammonium bromide, tetraphenylphosphonium bromide. The cocatalyst is used in an amount of from 0.01 mol% to 100 mol% and preferably from 0.1 to 50 mol%. If there are process-engineering advantages, the reaction can also be carried out in the cocatalyst as solvent.

In the process of the invention, catalyst turnover numbers in the order of 100,000 and more can be achieved for bromoaromatics as starting materials and values of 10,000 and more can be achieved for chylioroaromatics.

Owing to the catalyst activities and stabilities, it is thus possible in the process of the invention to use extremely small amounts of catalyst so that the catalyst costs are not the limiting cost factor compared to conventional Heck reactions for the corresponding process. In the process of the invention, catalyst contents used are from 1 to 2 mol% in exceptional cases, usually $\leq 1$ mol, particularly preferably $\leq 0.2$ mol%. Furthermoreyl, phosphite ligands are simpler to prepare and more stable in respect of oxidation reactions than the phosphine ligands used hitherto.

The process of the invention is particularly surprising and novel because no Heck reactions using palladium phosphite catalysts have been described in the past. This may be attributed to the fact that previous mechanistic conceptions for the Heck reaction assumed that an electron-rich palladium species is required as catalyst (A. de Meijere, F. E. Meyer, Angew. Chemie 1994, 106, 2473–2506, in particular p. 2475). Since phosphites are less electron-rich than phosphines, they were not regarded as suitable ligands for Heck reactions (C. A. Tolman, Chem. Rev. 1977, 77, 313–348, in particular pp. 343/344). The process of the invention shows for the first time that these conceptions are wrong.

The particular advantages of the novel catalyst system are the low oxidation sensitivity of the phosphite ligands compared to customarily used phosphine ligands. Furthermore, phosphites are, compared to phosphines, simpler to prepare and to modify, which is also reflected in the price of the corresponding ligands (e.g. DM 48 for 1 I of triethyl phosphite and DM 116 for 1 kg of triphenylphosphine from the same supplier).

The olefins prepared according to the invention can be used, inter alia, as UV absorbers, as intermediates for pharmaceuticals and agrochemicals, as ligand precursors for metallocene catalysts, as fragrances, active compounds and building blocks for polymers.

EXAMPLES

The following examples serve to illustrate the process of the invention, without restricting it thereto.

General Procedure

In a pressure tube (obtainable, for example, from Aldrich), 10 mmol of aryl halide or, in the case of Example 14, vinyl halide, 15 mmol of olefin, 12 mmol of sodium carbonate, 2.0 mmol of tetra-n-butylammonium bromide, an appropriate amount of phosphite and palladium(II) acetate and 500 mg of diethylene glycol di-n-butyl ether (as internal standard for GC analysis) were added under an argon atmosphere to 10 ml of dry N,N-dimethylacetamide. The tube was closed and hung in a hot silicone oil bath at 140 or 160° C. After 24 hours, the tube was allowed to cool to room temperature. The solids were dissolved in 10 ml of $CH_2Cl_2$ and 10 ml of 2 N hydrochloric acid. The organic phase was analyzed by gas chromatography. The products were isolated by distillation, crystallization from methanovacetone mixtures or by column chromatography (silica gel, hexane/ethyl acetate mixtures).

Catalyst mixture A: triethyl phosphite, P/Pd=100:1

Catalyst mixture B: tris(2,4-di-tert-butylphenyl) phosphite, P/Pd=10:1

Catalyst mixture C: tri-i-propyl phosphite, Pyl/Pd=10:1

Catalyst mixture D: triphenyl phosphite, P/Pd=10:1 (P=phosphite ligand)

TABLE 1

Overview of the examples according to the invention

| No. | Haloaromatic | Olefin | Bu$_4$NBr [mol %] | Catalyst | Pd [mol %] | Temperature [° C.] | GC yield [%] | TON |
|---|---|---|---|---|---|---|---|---|
| 1 | 4-chlorobenzo-trifluoride | styrene | 20 | A | 0.1 | 160 | 71 | 710 |
| 2 | 4-chlorobenzo-trifluoride | styrene | 0.2 | A | 0.001 | 160 | 15 | 15,000 |
| 3 | 4-chlorobenzo-trifluoride | styrene | 20 | B | 0.1 | 160 | 84 | 840 |
| 4 | 4-chlorobenzo-trifluoride | styrene[a] | 20 | C | 0.1 | 160 | 51 | 510 |
| 5 | 4-chlorobenzo-trifluoride | styrene | — | D | 0.1 | 160 | 47 | 470 |
| 6 | 4-chlorobenzo-trifluoride | N,N-dimethyl-acrylamide | 20 | B | 0.1 | 160 | 89 | 890 |
| 7 | 3-chlorobenzo-trifluoride | styrene | 20 | A | 0.1 | 160 | 79 | 790 |
| 8 | 2-chloro-5-nitrotoluene | n-butyl acrylate | 20 | A | 0.1 | 140 | 69 | 690 |
| 9 | 4-bromo-anisole | styrene | 20 | A | 0.1 | 140 | 66 | 660 |
| 10 | 4-bromo-anisole | styrene | — | B | 0.1 | 140 | 100 | 1,000 |
| 11 | 4-bromo-anisole | styrene | — | B | 0.001 | 140 | 30 | 30,000 |
| 12 | 2-bromo-6-methoxy-naphthalene | but-3-en-2-ol[a] | — | B | 0.1 | 160 | 66 | 660 |
| 13 | 4-bromo-acetophenone | styrene | — | B | 0.0001 | 140 | 75 | 750,000 |
| 14 | bromostyrene | styrene | — | B | 0.1 | 140 | 71 | 710 |

[a]sodium acetate instead of sodium carbonate

The examples demonstrate that in the process of the invention it is possible to achieve yields of at least 47% and in many cases more than 70% at increased turnover numbers or to achieve very high turnover numbers at more modest yields.

What is claimed is:

1. A process for preparing monofunctional, bifunctional or/and polyfunctional olefins of the formulae (Ia), (Ib), (Ic) or/and (Id),

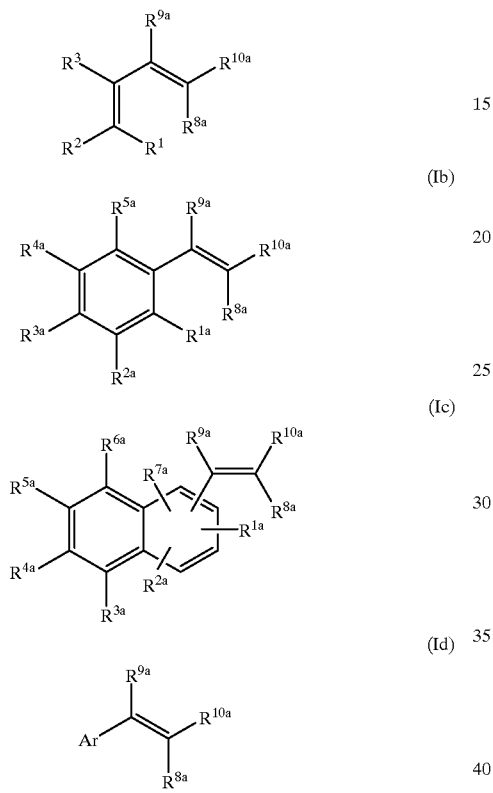

where
$R^1$ to $R^3$ are, independently of one another, hydrogen, $(C_1-C_8)$-alkyl, CN COOH, COO-alkyl-$(C_1-C_8)$, aryl-$(C_6-C_{10})$, COO-aryl-$(C_6-C_{10})$, CO-aryl-$(C_6-C_{10})$, O-alkyl-$(C_1-C_8)$, O—CO-alkyl-$(C_1-C_8)$, N-alkyl$_2$-$(C_1-C_8)$ and aryl is an aromatic radical containing up to 14 carbon atoms, where this radical may bear up to five substituents which are, independently of one another, hydrogen, $(C_1-C_8)$-alkyl, O-alkyl-$(C_1-C_8)$, OCO-alkyl-$(C_1-C_8)$, O-phenyl, phenyl, aryl, fluorine, chlorine, OH, NO$_2$, Si(alkyl-$(C_1-C_8))_3$,CN, COOH, CHO, SO$_3$H, NH$_2$, NH-alkyl-$(C_1-C_8)$, N-alkyl$_2$-$(C_1-C_8)$, P-alkyl$_2$-$(C_1-C_8)$, SO$_2$-alkyl-$(C_1-C_6)$, SO-alkyl-$(C_1-C_6)$, CF$_3$, NHCO-alkyl-$(C_1-C_4)$, COO-alkyl-$(C_1-C_8)$, CONH$_2$, CO-alkyl-$(C_1-C_8)$, NHCOH, NHCOO-alkyl-$(C_1-C_4)$, CO-phenyl, COO-phenyl, CHCH—CO$_2$-alkyl-$(C_1-C_8)$, P(phenyl)$_2$, CHCHCO$_2$H, PO-phenyl$_2$, POalkyl$_2$-$(C_1-C_4)$, PO$_3$H$_2$, PO(O-alkyl-$(C_1-C_6))_2$, SO$_3$-alkyl-$(C_1-C_4)$ where aryl is as defined above, and where $R^{1a}$ to $R^{7a}$ are, independently of one another, hydrogen, $(C_1-C_8)$-alkyl, O-alkyl-$(C_1-C_8)$, OCO-alkyl-$(C_1-C_8)$, O-phenyl, phenyl, aryl, fluorine, chlorine, OH, NO$_2$, Si(alkyl-$(C_1-C_8))_3$, CN, COOH, CHO, SO$_3$H, NH$_2$, NH-alkyl-$(C_1-C_8)$, N-alkyl$_2$-$(C_1-C_8)$, P-alkyl$_2$-$(C_1-C_8)$, SO$_2$-alkyl-$(C_1-C_6)$-alkyl-$(C_1-C_6)$, CF$_3$, NHCO-alkyl-$(C_1-C_4)$, COO-alkyl-$(C_1-C_8)$, CONH$_2$, CO-alkyl-$(C_1-C_8)$, NHCOH, NHCOO-alkyl-$(C_1-C_4)$, CO-phenyl, COO-phenyl, CHCH—CO$_2$-alkyl-$(C_1-C_8)$, P(phenyl)$_2$, CHCHCO$_2$H, PO-phenyl$_2$, POalkyl$_2$-$(C_1-C_4)$, PO$_3$H$_2$, PO(O-alkyl-$(C_1-C_6))_2$, SO$_3$-alkyl-$(C_1-C_4)$, where aryl is as defined above, and is a heteroaromatic, where the heteroaromatic Ar can be a substituted 5-, 6- or 7-membered ring containing, if desired, nitrogen, oxygen or sulfur atoms in the ring, where further aromatic, heteroaromatic and/or aliphatic rings can be fused onto the ring, and where the heteroaromatic can have substituents which are, independently of one another, hydrogen, $(C_1-C_8)$-alkyl, O-aryl, aryl, fluorine, chlorine, OH, NO$_2$, CN, CO$_2$H, CHO, SO$_3$H, NH$_2$, NH-alkyl-$(C_1-C_{12})$, N-alkyl$_2$-$(C_1-C_{12})$, CHCHCO$_2$H, NHCO-alkyl-$(C_1-C_{12})$, CO-alkyl-$(C_1-C_{12})$, NHCHO, COaryl, CO$_2$aryl, CF$_3$, CONH$_2$, POaryl$_2$, POalkyl$_2$-$(C_1-C_{12})$, Si(alkyl-$(C_1-C_2))_3$,O-alkyl-$(C_1-C_8)$, OCO-alkyl-$(C_1-C_8)$, O-phenyl, phenyl, NH-alkyl-$(C_1-C_4)$, COO-alkyl-$(C_1-C_8)$, NHCOO-alkyl-$(C_1-C_4)$, CO-phenyl, COO-phenyl, CHCH—CO$_2$-alkyl-$(C_1-C_8)$, PO-phenyl$_2$, PO$_3$H$_2$, SO$_3$-alkyl-$(C_1-C_4)$, SO$_2$-alkyl-$(C_1-C_4)$, SO-alkyl-$(C_1-C_4)$, where aryl is as defined above, and where $R^{8a}$ to $R^{10a}$ are, independently of one another, hydrogen, CN, CO$_2$H, CO$_2$-alkyl-$(C_1-C_8)$, CONH$_2$, CONH-alkyl-$(C_1-C_4)$, CON-(alkyl)$_2$-$(C_1-C_4)$, fluorine, CO$_2$-phenyl, alkyl-$(C_1-C_8)$yl, phenyl, aryl, PO(phenyl)$_2$, PO[alkyl-$(C_1-C_4)]_2$, CO-phenyl, CO-alkyl-$(C_1-C_4)$, O-alkyl-$(C_1-C_4)$, CONH-alkyl-$(C_1-C_8)$, CONH-alkyl-$(C_1-C_8)_2$,NH-alkyl-$(C_1-C_4)$, PO$_3$H$_2$, SO$_3$H, SO$_3$-alkyl-$(C_1-C_4)$, SO$_2$-alkyl-$(C_1-C_4)$, O-phenyl, where aryl is as defined above, by reacting haloaromatics, haloolefins or/and heterohaloaromatics of the formulae (IIa), (IIb), (IIc) or/and (IId)

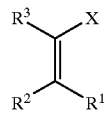

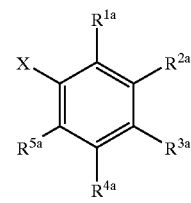

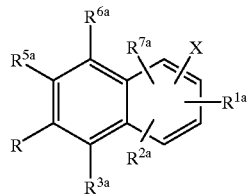

with olefins of the formula (III),

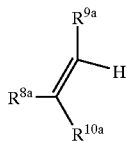
(III)

where, in the formulae of the type II and III, $R^1$ to $R^3$ and $R^{1a}$ to $R^{10a}$ are as defined above for the formulae of the type (I) and where X is iodine, bromine, chlorine, $OSO_2CF_3$, $OSO_2$-phenyl, $OSO_2$-tolyl, $OSO_2$-alkyl-$(C_1-C_8)$, wherein a mixture of a palladium(0) complex or a palladium(II) salt with phosphite ligands of the formulae (IVa) or/and (IVb),

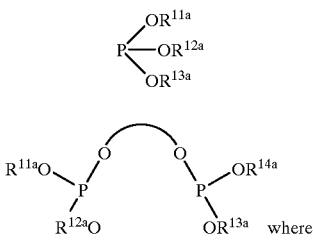
(IVa)

(IVb)

where the formula (IVb) represents a chelating phosphite ligand and where the radicals $R^{11a}$ to $R^{14a}$ are identical or different and are each, independently of one another, $(C_1-C_{18})$-alkyl or/and a substituted $(C_1-C_{18})$-alkyl group having the substituents hydrogen, O-alkyl-$(C_1-C_8)$, O—CO-alkyl-$(C_1-C_8)$, O-phenyl, phenyl, fluorine, chlorine, OH, $NO_2$, CN, COOH, CHO, $SO_3H$, $SO_2$-alkyl-$(C_1-C_8)$, SO-alkyl-$(C_1-C_8)$, $NH_2$, NH-alkyl-$(C_1-C_8)$, N-alkyl$_2$-$(C_1-C_8)$, NHCO-alkyl-$(C_1-C_4)$, $CF_3$, COO-alkyl-$(C_1-C_8)$, $CONH_2$, CO-alkyl-$(C_1-C_8)$, NHCOH, NHCOO-alkyl-$(C_1-C_4)$, CO-phenyl, COO-phenyl, CHCH—$CO_2$-alkyl-$(C_1-C_8)$, $CHCHCO_2H$, PO-phenyl$_2$, POalkyl$_2$-$(C_1-C_8)$, or the radicals $R^{11a}$ to $R^{14}$ are an aromatic Ar', where Ar' is a substituted phenyl, naphthyl, anthryl, phenanthryl or biphenyl radical or/and a 5-, 6- or 7-membered heteroaromatic containing, optionally nitrogen, oxygen or sulfur atoms in the ring, where the aromatics may contain up to ten substituents which are $(C_1-C_8)$-alkyl, OAr', Ar', fluorine, chlorine, OH, $NO_2$, CN, $CO_2H$, CHO, $SO_3H$, $NH_2$, NH-alkyl-$(C_1-C_{12})$, N-alkyl$_2$-$(C_1-C_{12})$, NHCO-alkyl-$(C_1-C_{12})$, CO-alkyl-$(C_1-C_{12})$, NHCHO, COAr', $CO_2$Ar', $CF_3$, $CONH_2$, $CHCHCO_2H$, POAr's, POalkyl$_2$-$(C_1-C_{12})$, Si(alkyl-$(C_1-C_{12})$)$_3$,O-alkyl-$(C_1-C_8)$, OCO-alkyl-$(C_1-C_8)$, O-phenyl, phenyl, COO-alkyl-$(C_1-C_8)$, NHCOO-alkyl-$(C_1-C_4)$, CO-phenyl, COO-phenyl, CHCH—$CO_2$-alkyl-$(C_1-C_8)$, PO-phenyl$_2$, $PO_3H_2$, $SO_3$-alkyl-$(C_1-C_4)$, $SO_2$-alkyl-$(C_1-C_4)$, SO-alkyl-$(C_1-C_8)$, where the carbon bridge of the phosphite ligand $C_2$ to $C_4$ may have up to four substituents which are identical or different and are, hydrogen, $(C_1-C_4)$-alkyl, O-alkyl-$(C_1-C_4)$, OH, aryl or/and phenyl, where aryl is as defined above.

2. The process as claimed in claim 1, for preparing compounds of the formula (Id), wherein the heteroaromatics ArX of the formula (IId) which are used are substituted heterohaloaromatics having up to four heteroatoms in the ring, where the substituents can be identical or different and be, independently of one another, hydrogen, $(C_1-C_8)$-alkyl, O-aryl, aryl, fluorine, chlorine, OH, $NO_2$, CN, $CO_2H$, CHO, $SO_3H$, $NH_2$, NH-alkyl-$(C_1-C_{12})$, N-alkyl$_2$-$(C_1-C_{12})$, NHCO-alkyl-$(C_1-C_{12})$,CO-alkyl-$(C_1-C_{12})$, NHCHO, COaryl, $CO_2$aryl, $CF_3$, $CONH_2$, POaryl$_2$, POalkyl$_2$-$(C_1-C_{12})$, Si(alkyl-$(C_1-C_{12})$)$_3$,O-alkyl-$(C_1-C_8)$, OCO-alkyl-$(C_1-C_8)$, O-phenyl, phenyl, COO-alkyl-$(C_1-C_8)$, NHCOO-alkyl-$(C_1-C_4)$, CO-phenyl, COO-phenyl, CHCH—$CO_2$-alkyl-$(C_1-C_8)$, PO-phenyl$_2$, $PO_3H_2$, $SO_3$-alkyl-$(C_1-C_4)$, $SO_2$-alkyl-$(C_1-C_4)$, SO-alkyl-$(C_1-C_4)$, where aryl is as defined above, and $R^{8a}$ to $R^{10a}$ are identical or different and are, independently of one another, hydrogen, CN, $CO_2H$, phenyl, $CO_2$alkyl-$(C_1-C_8)$, $CONH_2$, F, O-alkyl-$(C_1-C_4)$, alkyl-$(C_1-C_8)$, NH-alkyl-$(C_1-C_4)$.

3. The process as claimed in claim 1, wherein the olefins prepared are ones of the formula (Ia) in which $R^1$ to $R^3$ is hydrogen, $(C_1-C_4)$-alkyl or/and phenyl.

4. The process for preparing compounds of the formulae (Ia), (Ib), (Ic) or/and (Id) as claimed in claim 1, wherein $R^1$ to $R^3$ and $R^{1a}$ to $R^{7a}$ are, independently of one another, hydrogen, $(C_1-C_8)$-alkyl, O-alkyl-$(C_1-C_8)$, O—CO-alkyl-$(C_1-C_8)$, N-alkyl$_2$-$(C_1-C_8)$, phenyl, aryl, fluorine, chlorine, $NO_2$, CN, COOH, CHO, $SO_2$-alkyl-$(C_1-C_4)$,NH-$(C_1-C_8)$-alkyl, N[$(C_1-C_8)$-alkyl]$_2$, COO-$(C_1-C_8)$-alkyl, $CONH_2$, CO-$(C_1-C_8)$-alkyl, CO-phenyl or/and PO(phenyl)$_2$, where aryl is as defined above, and $R^{8a}$ to $R^{10a}$ are, independently of one another, hydrogen, CN, $CO_2H$, $CO_2$-alkyl-$(C_1-C_8)$, $CONH_2$, F, O-alkyl-$(C_1-C_4)$, alkyl-$(C_1-C_8)$, NH-alkyl-$(C_1-C_4)$, CONH-alkyl-$(C_1-C_8)$, CON[alkyl-$(C_1-C_8)$]$_2$, phenyl or/and aryl, where aryl is as defined above.

5. The process as claimed in claim 1, where said solvent is an inert organic solvent, water or mixture thereof.

6. The process as claimed in claim 1, wherein the reaction proceeds at temperatures of from 20 to 200° C. with the pressure being able to be up to 100 bar.

7. The process as claimed in claim 1, wherein HX which is eliminated in the reaction is neutralized by addition of a base.

8. The process as claimed in claim 1, wherein the palladium catalysts (IV) used are generated in situ from palladium(II) salts and the corresponding phosphite ligands.

9. The process as claimed in claim 1, wherein the palladium catalysts (IV) used are used directly as palladium(0) phosphite complexes.

10. The process as claimed in claim 1, wherein palladium-containing precursors used are palladium(II) acetate, palladium(II) chloride, palladium(II) bromide, lithium tetrachloropalladate, palladium(II) acetylacetonate, palladium(0)-dibenzylidene-acetone complexes, tetrakisylitylriphenylphosphine)palladium(0), bis(tri-O-tolyl-phosphine)palladium(0), palladium(II) propionate, bis (acetonitrile)palladium(II) chloride, bis(triphenylphosphine) palladium(II) dichlorideyl, palladium(0)-tricyclohexylphosphine-(diallyl ether) complex, bis (tricyclohexylphosphine)-palladium(0), bis(benzonitrile) palladium(II) chloride or/and further palladium(0) and palladium(II) complexes.

11. The process as claimed in claim 1, wherein use is made of a chelating phosphite ligand whose carbon bridge $C_2$ to $C_4$ has up to four identical or different substituents.

12. The process as claimed in claim 1, wherein the catalyst is used in a palladium:ligand ratio of from 1:2 to 1:200.

13. The process as claimed in claim 1, wherein a cocatalyst, is added to the palladium phosphite catalyst.

14. The process as claimed in claim 1, wherein the cocatalyst is added in an amount of from 0.01 mol % to 50 mol %.

15. The process as claimed in claim 1, wherein the reaction is carried out in the cocatalyst as solvent.

16. The process as claimed in claim 1, wherein catalyst contents of $\leq 2$ mol%, are used.

17. The process as claimed in claim 2, wherein the heterohaloaromatics ArX of the formula (IId) which are used are substituted heterohaloaromatics having up to four heteroatoms and the heteroatoms are N, O, or S or a mixture thereof.

18. The process as claimed in claim 2, wherein the heterohaloaromatics ArX of the formula (IId) are pyridines, pyrimidines, oxazoles, imidazoles, pyrazines, quinolines, indoles, furans, benzofurans or/and thiophenes.

19. The process as claimed in claim 14, wherein the catalyst is used in a palladium:ligand ratio of from 1:5 to 1:200 and the cocatalyst is added in an amount of from 0.1 to 50 mol %.

* * * * *

UNITED STATES PATENT AND TRADEMARK OFFICE
CERTIFICATE OF CORRECTION

PATENT NO. : 6,291,383 B1
DATED : September 18, 2001
INVENTOR(S) : Zapf et al.

It is certified that error appears in the above-identified patent and that said Letters Patent is hereby corrected as shown below:

<u>Title page,</u>
Item [57], ABSTRACT,
Line 3, after "Formula (ID), "...COO-aryl-($C_6$-$C_{10}$), CO-aryl-" should read as -- ...COO-aryl-($C_6$-$C_{10}$), CO-aryl- --.

<u>Column 10,</u>
Line 1, "...$SO_2$-alkyl-($C_1$-$C_6$)-alkyl-($C_1$-$C_6$),.." should read as -- ...$SO_2$-alkyl-($C_1$-$C_6$), SO-alkyl-($C_1$-$C_6$),... --.
Line 21, "...Si(alkyl-($C_1$-$C_2$))$_3$,)-" should read as -- ...Si(alkyl-($C_1$-$C_{12}$))$_3$,) --.
Line 31, "...alkyl-($C_1$-$C_8$)yl,..." should read as -- ...alkyl-($C_1$-$C_8$),... --.
Lines 33-34, "...CONH-alkyl-($C_1$-$C_8$)$_2$,NH-alkyl-($C_1$-$C_4$),..." should read as -- ...CON[-alkyl-($C_1$-$C_8$)]$_2$, NH-alkyl-($C_1$-$C_4$),... --.

<u>Column 11,</u>
Line 45, "or the radicals $R^{11a}$ to $R^{14}$ are an...." should read as -- or the radicals $R^{11a}$ to $R^{14a}$ are an.... --.
Line 61, "($C_1$-$C_8$),..." should read as -- ($C_1$-$C_4$),... --.

<u>Column 12,</u>
Line 56, "palladium(0)-dibenzylidene-acetone complexes," should read as -- palladium(0)-dibenzylideneacetone complexes --.
Line 57, "tetrakisylitylriphenylphosphine)palladium(0),..." should read as -- tetrakis(triphenylphosphine)palladium(0) --.
Lines 57-58, "...bis(tri-O-tolyl-phosphine)palladium(0),..." should read as -- ...bis(tri-O-tolylphosphine)palladium(0),... --.
Line 60, "...dichlorideyl,..." should read as -- ...dichloride, --.

Signed and Sealed this

First Day of July, 2003

JAMES E. ROGAN
*Director of the United States Patent and Trademark Office*